United States Patent
Becker et al.

(10) Patent No.: US 12,031,989 B2
(45) Date of Patent: *Jul. 9, 2024

(54) PREPARING LIVE MICROBIAL SAMPLES AND MICROORGANISMS FOR SUBSEQUENT MASS SPECTROMETRIC MEASUREMENT AND EVALUATION

(71) Applicant: Bruker Daltonics GmbH & Co. KG, Bremen (DE)

(72) Inventors: Karsten Becker, Laer (DE); Evgeny Idelevich, Münster (DE)

(*) Notice: Subject to any disclaimer, the term of this patent is extended or adjusted under 35 U.S.C. 154(b) by 0 days.

This patent is subject to a terminal disclaimer.

(21) Appl. No.: 17/823,318

(22) Filed: Aug. 30, 2022

(65) Prior Publication Data

US 2022/0412987 A1    Dec. 29, 2022

Related U.S. Application Data

(63) Continuation of application No. 16/464,288, filed as application No. PCT/DE2016/100561 on Nov. 30, 2016, now Pat. No. 11,480,579.

(51) Int. Cl.
*G01N 33/68* (2006.01)
*C12Q 1/18* (2006.01)

(52) U.S. Cl.
CPC ............ *G01N 33/6848* (2013.01); *C12Q 1/18* (2013.01); *G01N 33/6851* (2013.01); *G01N 2560/00* (2013.01); *G01N 2800/44* (2013.01)

(58) Field of Classification Search
CPC ........... G01N 33/6848; G01N 33/6851; G01N 2560/00; G01N 2800/44; C12Q 1/18
See application file for complete search history.

(56) References Cited

U.S. PATENT DOCUMENTS

| | | | | |
|---|---|---|---|---|
| 2010/0260869 A1* | 10/2010 | Gogotsi | ................ | A01N 59/00 424/661 |
| 2010/0285572 A1* | 11/2010 | Salter | .................... | C12M 33/02 435/32 |
| 2015/0086971 A1* | 3/2015 | Botma | ............. | G01N 35/00029 435/286.2 |
| 2017/0211123 A1* | 7/2017 | Ramjeet | ............. | G01N 33/6851 |

FOREIGN PATENT DOCUMENTS

| | | | | |
|---|---|---|---|---|
| WO | WO-2012023845 A1 * | 2/2012 | ............... | C12Q 1/02 |
| WO | WO-2016016580 A1 * | 2/2016 | ............... | C12Q 1/04 |

OTHER PUBLICATIONS

Croxatto, A et al. Applications of MALDI-TOF mass spectrometry in clinical diagnostic microbiology. FEMS Microbiol. Rev. 2012. 36: 380-407. (Year: 2012).*

Iso-Sensitest™ broth Product Specification sheet. BT-SPEC-0158. [online] Fisher Scientific, 2008 [retrieved on Dec. 17, 2023]. Retrieved from the Internet: <URL: https://assets.fishersci.com/TFS-Assets/MBD/Specification-Sheets/BT-SPEC-0158.pdf>. (Year: 2008).*

Iso-Sensitest(TM) Broth CM0473 Product Specification. ThermoFisher Scientific. 4 pages. No date. (Year: NA).*

* cited by examiner

*Primary Examiner* — Adam Weidner
*Assistant Examiner* — Susan E. Fernandez
(74) *Attorney, Agent, or Firm* — Benoît & Côté Inc.

(57) ABSTRACT

The invention relates to a method for the preparation of living, microbial samples and microorganisms for subsequent mass spectrometric measurement and evaluation. Findings which can be derived from such a measurement can particularly serve the faster identification of microorganisms in the microbial sample according to species/subspecies and/or the fast determination of resistance/sensitivity of the microorganisms to antimicrobial substances and/or the further characterization of microorganisms, for example in respect of pathogenicity, virulence and metabolism. According to a preferred embodiment of the invention, the preparation particularly takes place directly on a mass spectrometric sample support.

20 Claims, 8 Drawing Sheets

PREPARING LIVE MICROBIAL SAMPLES AND MICROORGANISMS FOR SUBSEQUENT MASS SPECTROMETRIC MEASUREMENT AND EVALUATION

FIELD OF THE INVENTION

The invention relates to methods for the preparation of living, microbial samples and microorganisms for subsequent mass spectrometric measurement and evaluation. Findings which can be derived from such a measurement can particularly serve the faster identification of microorganisms in the microbial sample according to species/subspecies and/or the fast determination of resistance/sensitivity of the microorganisms to antimicrobial substances and/or the further characterization of microorganisms, for example in respect of pathogenicity, virulence and metabolism. According to a preferred embodiment of the invention, the preparation particularly takes place directly on a mass spectrometric sample support.

BACKGROUND TO THE INVENTION

Infectious diseases still represent one of the main problems in medicine. Infections can occur independently, but develop particularly as complications of other illnesses or as a consequence of immunosuppressive therapies and/or the use of foreign materials on the patient. In recent years, the progress made in modern medicine and the associated increase in complicated surgical procedures and immunosuppressive therapies and the use of foreign bodies have been among the factors responsible for an increase in rates of infection. To be mentioned in this context are transplants of solid organs and bone marrow transplants, for example.

The increase in multi-resistant pathogens in particular gives cause for concern; for example, bacteria (incl. MRSA—methicillin-resistant *Staphylococcus aureus*; VRE—vancomycin-resistant enterococci; ciprofloxacin-, meropenem- or tobramycin-resistant *Pseudomonas aeruginosa*) or fungi (incl. fluconazole- or voriconazole-resistant *Candida albicans*). The infections caused by these pathogens are particularly difficult to treat with antimicrobial substances. Since the antimicrobial drugs initially administered as part of a so-called "empirical" or "calculated" therapy usually do not include multi-resistant pathogens in their activity spectrum, it is crucial for the success of the treatment that the resistances are detected at an early stage. A rapid identification of resistant microorganisms allows a timely switch to antimicrobial substances which are effective against these pathogens. For the sake of simplicity, they are called antibiotics below; this term is taken to mean not only substances which are effective against bacteria, but also drugs against fungi and other microorganisms. Such a switch to a correct antimicrobial therapy at an early stage can be crucial for the success of the treatment.

There is currently a particular lack of phenotypic (i.e. culture-based) test systems or individual tests which can provide a sensitivity test result within only a few hours. Phenotypical resistance means that the microorganism grows despite the presence of an antibiotic. With phenotypical antibiotic sensitivity, growth is inhibited in the presence of the antibiotic under test if this is administered in a sufficient concentration. Phenotypical sensitivity testing represents the gold standard. One reason is that the test results are generated regardless of the underlying resistance mechanisms. Although certain resistance genes can be detected with the aid of molecular biology within a short time, by polymerase chain reaction—PCR, for example, this detection is only possible for some of the resistance mechanisms; the other resistance mechanisms are not detected. Moreover, such molecular tests only detect already known, genetically coded resistance mechanisms. It is thus not possible to make a reliable statement about the sensitivity of a pathogen to an antibiotic unless a specific resistance gene is detected. In addition, these methods by no means always allow a reliable prediction to be made about the phenotypical resistance if a resistance gene is detected. This is because the manifestation of the gene expression can vary; and the microorganism can react with phenotypical sensitivity to the antibiotic despite the presence of the gene.

Furthermore, gene detection is not possible for a great many of the resistance mechanisms. The methods which are able to rapidly detect specific resistance mechanisms by virtue of their phenotype include, for example, the detection of the β-lactamases produced by some bacteria. β-lactamases are bacterial enzymes which can cleave β-lactam antibiotics and thus make them ineffective. The detection can be done by detecting the β-lactam cleavage, for example by a pH indicator changing color or with the aid of MALDI-TOF MS (matrix-assisted laser desorption/ionization—MALDI; TOF—time-of-flight; mass spectrometry—MS). MALDI-TOF MS involves the mass-spectrometric determination of the uncleaved β-lactam and/or its cleavage products. Although these methods can be advantageous in certain situations, they have the general disadvantage that only one specific resistance mechanism is detected and it is not possible to make a general, definitive statement about the sensitivity or resistance of a pathogen.

There is therefore an urgent need for methods which, on the one hand, allow growth-based, phenotypic sensitivity testing and thus a general statement, as is the case with the usual test methods, but on the other hand are significantly faster than the usual methods. The general objective for such rapid tests would be to provide the result within only a few hours, i.e. within 1-4 hours, for example. The achievability of these target times depends firstly on the test method, and secondly on the characteristics of the microorganisms to be tested; for example, their rate of growth.

"MBT ASTRA", the recently developed MALDI-TOF MS-based method for sensitivity testing, which uses an internal standard for the quantification of microbial growth, demonstrates that general growth-based sensitivity testing by means of MALDI-TOF MS is feasible (Lange et al., Journal of Clinical Microbiology, December 2014, Volume 52, Number 12, p. 4155-4162; and K. Sparbier et al./Methods 104 (2016) 48-54). However, the method in the form described so far requires several processing steps, which means a large amount of work in the laboratory. This effort can lower the acceptance of the method and thus hinder the introduction of this method, which is basically advantageous for the patient, in routine diagnostics, or possibly even prevent it altogether.

Given the explanations above, there is a need to provide methods whereby the preparation of living, microbial samples for subsequent mass spectrometric measurement can be simplified and accelerated. Further objectives to be achieved by the invention are immediately clear to the person skilled in the art from reading the disclosure below.

SUMMARY OF THE INVENTION

The methods described here represent an alternative method for a very fast and simple MS-based microbial measurement, for example for the identification of species/ subspecies and/or resistance/sensitivity testing and/or further pathogen characterization. The disclosure relates in particular to the method of sample processing/preparation and also to data evaluation algorithms.

According to a first preferred aspect, the present disclosure relates to a method for the preparation of living, microbial samples for subsequent mass spectrometric measurement, comprising the following Steps: (a) Provide a flat sample support containing several sample spots; (b) deposit at least one living, microbial sample in a droplet of nutrient medium on at least one of the sample spots; (c) place the sample support in an incubation chamber with a defined atmosphere for a predetermined period of time to stimulate the growth of microorganisms; (d) remove residual liquid from the droplet of nutrient medium after the predetermined period of time to expose a deposit of microorganisms on the sample spot; (e) prepare the sample spot for a desorbing ionization; (f) transfer the sample support into a desorption ion source of a mass spectrometer, generate ions from the prepared sample spot and acquire at least one corresponding mass spectrum; and (g) compare the mass spectrum acquired with a reference data set to determine at least one characteristic of the microbial sample.

The first preferred aspect of the disclosure is based in particular on the new and surprising finding that a flat mass spectrometric sample support, serving as the substrate for the ionization of the processed samples in a suitable ion source, can already serve as the substrate for growth-promoting incubation of microorganisms in a preceding step. This dual function makes the workflow in the laboratory much easier, and shortens the time needed for the diagnostic procedure, because complicated and error-prone manual sample transfer steps can be avoided and there is no need to have separate preparation vessels such as microtitration plates. This procedural simplification can help fast, reliable and comprehensively validated mass spectrometric measurement of microorganisms to become established in clinical diagnostics.

In various embodiments, the reference data set can comprise reference spectra which are taken from a library of previously acquired mass spectra. Here, for the process of identification, the at least one characteristic from Step (g) can comprise species or subspecies of microorganisms in the microbial sample. In this simple version, the droplet of nutrient medium acts as a pure growth reactor on the mass spectrometric sample support. Specialists will recognize that microorganisms can multiply more quickly in a liquid than on a flat nutrient medium, such as an agar layer in a Petri dish, because, amongst other factors, they are bathed on all sides with nutrient medium. Thus, the proposed method affords a time advantage which can prove crucial for the survival of the patient in the clinical environment.

In specific cases, the reference data set can be derived from the mass signals contained in the mass spectrum acquired in Step (f), which do not originate from microorganisms. Mass signals of one (or more) reference substance (s) (internal standard), which are added as the microbial sample is being prepared and which can be used for the quantification, are stated as an example.

In preferred embodiments, the same microbial sample is applied to several sample spots in parallel in Step (b). The droplets of nutrient medium sometimes contain an antimicrobial substance and sometimes do not. A mass spectrometric sample support is particularly suitable for extensive resistance/sensitivity testing because it offers sufficient space to simultaneously monitor the growth of microorganisms in the presence of different antimicrobial substances (or the same antimicrobial substance at different concentrations). The question as to whether a microorganism exhibits a sensitive reaction to a specific antimicrobial substance (or the concentration at which it begins to do so), which would indicate its effectiveness as a drug, for example, can therefore be clarified very rapidly and reliably.

In special embodiments of the method, several droplets of nutrient medium with an antimicrobial substance can sometimes contain an enzyme inhibitor and sometimes not. It can be of great clinical and therapeutic interest when a β-lactamase inhibitor is used as an enzyme inhibitor. This extension of resistance/sensitivity testing is informative in regard to β-lactamase-based resistance if growth of the microorganism under investigation is not inhibited by the presence of the β-lactam antibiotic, but is inhibited in the presence of a combination of β-lactam antibiotic and β-lactamase inhibitor.

In various embodiments, the reference data set can be a very recently acquired mass spectrum of a sample spot, to which a droplet of nutrient medium without any antimicrobial substance or enzyme inhibitor has been applied in Step (b); and for the purpose of characterization, at least one characteristic from Step (g) can comprise a resistance/sensitivity of microorganisms in the microbial sample to the antimicrobial substance or to a combination of antimicrobial substance and enzyme inhibitor. It is thus possible to determine, in particular the minimum inhibitory concentration of an antibiotic with respect to the microorganisms by applying several droplets of nutrient medium, each with different concentrations of the antimicrobial substance (and/or the inhibitor, if applicable), in Step (b) and assessing the degree of effectiveness along a series of increasing or decreasing concentrations.

In a further embodiment, the reference data set can be a mass spectrum of a sample spot on a second sample support, where the microorganisms for the mass spectrum used as the reference data set were incubated for a shorter time, or possibly not incubated at all. The microbial sample here is preferably applied to the sample spot in a droplet of nutrient medium without any antimicrobial substance or without a combination of antimicrobial substance and enzyme inhibitor. The quantities of microbial cells applied initially to the sample spots for the mass spectra of the microbial sample and the reference data set are preferably the same.

It is preferable for the at least one characteristic in Step (g) to be derived from a difference in the microorganism growth, which is reflected in the manifestation or intensity of the microorganism-specific mass signal signature in the acquired mass spectrum, depending on whether or not it was possible to find a growth inhibition caused by an antimicrobial substance alone or in combination with an enzyme inhibitor. In a simple version, the microorganism growth can be assessed on the basis of a successful identification of the species if the quantity of microorganisms in the microbial sample measured before the incubation is not sufficient for a reliable identification. The MALDI Biotyper® algorithm can be stated as an example of a well-known identification method, which confirms an acceptably reliable identification of a species of a microorganism, as long as the calculated similarity index (so-called "log(Score)") is 1.7 or higher. A high degree of reliability is achieved with similarity indices of 2.0 or higher.

In various embodiments, the microbial sample in Step (b) can be dosed in the droplet of nutrient medium such that a quantity lies slightly below the detection limit of the mass spectrometric measurement. In particular, the length of time the sample support has to remain in the incubation chamber to stimulate microorganism growth can thus be reduced to a minimum. Growth which attains the detection limit, or slightly exceeds it, can in itself be interpreted as an indication for the presence or a characteristic of the microorganism compared to a measurement which contains no informative data apart from background signals.

In various embodiments, the temperature and humidity in the incubation chamber in Step (c) can be set to around 36° C. (this is possibly necessary or even prescribed for incubation or for sensitivity testing) and close to saturation, respectively, to create optimum or required growth conditions for the microorganisms under investigation. The objective should generally be to create conditions in the incubation chamber which cause differences in growth to be revealed most clearly. The temperature of 36° C. roughly corresponds to the temperature of the human body and is suitable for those microorganisms which have specialized in humans as their host. In veterinary, food or environmental diagnostics, for example, it is quite possible for other temperatures to be identified as being the most suitable ones, depending on which host or ambient environment is preferred by the microorganism. The high air humidity of close to 100% serves in particular to prevent the droplet of nutrient medium from evaporating prematurely so that the volume of liquid available for the growth of microorganisms remains roughly the same over the pre-determined period of time, which usually amounts to several hours, during which the sample support is in the incubation chamber (generally 1-18 hours).

In various embodiments, the removal of residual liquid (after the incubation step) may involve dabbing off the droplet supernatant with an absorbent material or pipetting it off. These versions have the advantage that residues of the substances present in the droplet of nutrient medium are largely removed from the sample spot together with the liquid, which can reduce the chemical background in the subsequent mass spectrometric measurement. However, it is also possible to make the liquid evaporate in a short period of time, for example with the aid of a hot air blower. In this case, the substances in the liquid nutrient medium precipitate on the microorganism deposit and are subsequently prepared together with it, at least partially, for the subsequent mass spectrometric measurement.

In different embodiments, the preparation in Step (e) can involve a preparatory extraction of microbial proteins/peptides from the microorganism deposit and/or washing the microorganism deposit and/or embedding the microorganism deposit in a laser light-absorbing matrix substance for the purpose of subsequent ionization by matrix-assisted laser desorption (MALDI). In the case of extraction, the number of microorganism-specific mass signals in the mass spectrum acquired can be increased, and hence the informative value of the measurement enhanced; this is true especially when the aim is identification by species/subspecies of the microorganism under investigation. One or more washing steps are particularly suitable for removing the almost omnipresent salts from the microorganism deposit, which can otherwise diminish the ionization efficiency. The method of preparation can thus be optimized further. Examples for matrix substances are 2,5-dihydroxybenzoic acid, sinapic acid or α-cyano-4-hydroxycinnamic acid. The MALDI method has proven to be a very important and reliable tool in the ion-based investigation of microorganisms. At the same time, it allows pulsed ion generation, which is ideal to acquire mass spectra with a time-of-flight dispersion.

It is also conceivable, however, that other types of desorption ionization, which do not require the application of a matrix substance, can be used with the method described; for example desorption electrospray ionization (DESI) or ionization by means of secondary ion mass spectrometry (SIMS). In very specific cases, the preparation in Step (e) may comprise only a short waiting time of a few minutes, for example, without any further treatment of the microorganism deposit.

Advantageously, the mass spectra in Step (f) are acquired with a time-of-flight dispersion. Time-of-flight mass spectrometers can currently be viewed as the "gold standard" in both clinical and non-clinical analysis of microorganisms due to their high resolution, fast measurement time and wide mass acceptance. Examples of mass spectrometers which operate according to the time-of-flight principle are those in the commercially available Microflex® series from Bruker Daltonik GmbH.

In various embodiments, the microbial sample (i) can be dispensed in Step (b) as a suspension in the droplet of nutrient medium on the at least one sample spot or (ii) first deposited in cellular form on the at least one sample spot and subsequently immersed in a dispensed droplet of nutrient medium. In further versions, the antimicrobial substances (and the enzyme inhibitors also, where appropriate) can be applied onto the sample spot either together with the microbial sample and/or the nutrient medium or separately therefrom. In principle, it is also conceivable to reverse the order of the deposition and dispensing so that first a droplet is dispensed, into which the microbial sample is then introduced.

According to a further preferred aspect, the present disclosure relates to a method for the preparation of microorganisms for subsequent mass spectrometric measurement, comprising the following Steps: (a) provide a flat sample support containing several sample spots, for example an MSP 48/96 target polished steel BC from Bruker Daltonik GmbH; (b) deposit intact microorganisms, cultured and/or separated away from the sample support, in a droplet of nutrient medium on at least one of the sample spots of the flat sample support, preferably with a nanopipette or a micropipette; the quantity of the droplets transferred can amount to between 1 and 10 microliters; (c) keep the flat sample support for a predetermined resting period, preferably around 10 to 60 minutes, to allow a microorganism deposit to form on the sample spot; (d) remove residual liquid from the droplet of nutrient medium after the predetermined resting period in order to expose the deposit of microorganisms; (e) prepare the sample spot for a desorbing ionization, preferably with a MALDI matrix substance; (f) transfer the sample support into a desorption ion source of a mass spectrometer, generate ions from the prepared sample spot and acquire at least one corresponding mass spectrum; and (g) compare the mass spectrum acquired with a reference data set to determine at least one characteristic of the microorganisms.

The inventors have ascertained that a microorganism deposit on a flat surface can form after only a relatively short resting period of up to one hour, such that the microorganisms sedimented there in a kind of "biofilm" can be gently freed from residual liquid and be reliably detected by subsequent mass spectrometric measurement. Exploiting this surprising finding, the cultivation (or incubation) of microorganisms for the purpose of growth promotion and the preparation for mass spectrometric measurement, which are carried out on the same mass spectrometric sample support according to the first aspect of the disclosure, can be carried out on different substrates according to the second aspect. This spatial separation opens up possible applications particularly in the automation of workflows, since in a clinical environment an automated culture protocol can possibly be carried out more easily in vessels such as the wells of a standardized microtitration plate than on a flat surface, such as a MALDI-TOF MS support. In principle, the explanations of the method according to the first aspect also apply to the method according to the second aspect if they can be made compatible with it.

In various embodiments, the reference data set can have reference spectra which are taken from a library of previously acquired mass spectra and, for the identification, the at least one characteristic from Step (g) comprises species or subspecies of the microorganisms.

In various embodiments, the microorganisms can be cultured in a liquid nutrient medium in at least one vessel away from the flat sample support before being applied in Step (b), and transferred from there onto the sample spot; the cultivation preferably takes around 4 to 24 hours in a conditioned/temperature-controlled incubator. The cultivation is particularly useful for sensitivity testing of the microorganisms—preferably in both the presence and absence of an antibiotic, as has been described above. For an identification or determination of specific proteins in the mass spectrum, which could point to specific virulence factors or other microbial characteristics, a cultivation is not absolutely necessary, and therefore does not need to be part of the method which is protected. It is possible to use an already existing microorganism suspension, for example one which has been produced as a consequence of other processes in the laboratory. To give an example: a suspension of bacteria, for example, is produced by dissolving the bacteria colonies present on agar plates in liquid; this could be preceded by a cultivation of the bacteria on a solid medium such as agar, which allows the colonies to grow (they could already have been available in this form for days). A further example: the MALDI Sepsityper® Kit uses the liquid from positive blood culture bottles, which contain the blood of septic patients and liquid medium and, in the positive case, also cultured pathogens. The kit enriches the pathogen from this positive liquid further by means of a lysis/centrifugation method—with subsequent protein extraction and MALDI measurement of the proteins. Alternatively, several microliters of the positive blood culture liquid can be applied onto a spot. Even without incubation using added heat, but simply at room temperature, the microorganism cells (i) will sediment and (ii) adhere to the surface of the support; (iii) furthermore, most species will even multiply to a small extent at room temperature.

In various further embodiments, the same microorganisms can be cultured in several (external) vessels, and an antimicrobial substance can be added to the liquid nutrient medium in some cases but not in others. In addition, an enzyme inhibitor can sometimes be added to the liquid nutrient medium in different vessels with added antimicrobial substance, and sometimes not. One example is a β-lactamase inhibitor.

In various embodiments, the reference data set can be a recently acquired mass spectrum of a sample spot on which there is a microorganism deposit which originated from a liquid nutrient medium without antimicrobial substance or enzyme inhibitor, and for the purpose of characterization, the at least one characteristic from Step (g) can comprise a sensitivity of the microorganisms with respect to the antimicrobial substance or a combination of antimicrobial substance and enzyme inhibitor. In a special version, the same microorganisms can be cultured in different (external) vessels with liquid nutrient medium at different concentrations in each case, and for the purpose of characterization, the at least one characteristic from Step (g) can comprise a minimum inhibitory concentration of the antimicrobial substance with respect to the microorganisms.

It is preferable for the at least one characteristic in Step (g) to be derived from a difference in the microorganism growth, which can manifest itself in a difference between reliable and failed identification with the MALDI Biotyper® algorithm, for example.

At the start of the cultivation, the microorganisms can be dosed such that a quantity is slightly below the detection limit of the mass spectrometric measurement, for example at around $10^5$ cfu per milliliter of nutrient medium, particularly leading to a concentration of at least around 100 microorganisms per spot.

In various embodiments, the removal of the residual liquid from the flat sample support in Step (d) may involve dabbing off the droplet supernatant with an absorbent material or pipetting it off.

The preparation in Step (e) can comprise a preparatory extraction of microbial proteins/peptides from the microorganism deposit on the flat sample support and/or washing the microorganism deposit and/or embedding the microorganism deposit in a laser light-absorbing matrix substance, in order to subsequently be ionized by matrix-assisted laser desorption (MALDI) in Step (f).

The mass spectra in Step (f) are preferably acquired with time-of-flight dispersion (in a time-of-flight-mass spectrometer).

In various embodiments, the microorganisms can be (i) dispensed into the (external) vessel as a suspension in the liquid nutrient medium or (ii) first introduced into the (external) vessel in cellular form, after which liquid nutrient medium is added; the quantity of nutrient medium can be between 10 and 100 microliters, for example.

In various embodiments, a well (or several wells) in a microtitration plate can be used as the (external) vessel(s) for the cultivation. As an alternative, the sample support plate from Step (a) can be divided into a first flat section with flat sample spots and a second section with wells on the surface. The wells are used as (external) vessels (away from the first flat section) and the intact microorganisms grown therein in Step (b) are transferred from there onto flat sample spots in the first flat section.

BRIEF DESCRIPTION OF THE ILLUSTRATIONS

The invention can be better understood by referring to the following illustrations. The elements in the illustrations are not necessarily to scale, but are primarily intended to illustrate the principles of the invention (largely schematically). In the illustrations, the same reference numbers designate corresponding elements in the different views.

FIG. 1 is a schematic of an embodiment for a mass spectrometer 10 with linear-axial flight path 2, which ends at a detector 4, and upstream ion source 6 for the matrix-assisted laser desorption (MALDI), as is often used in mass spectrometric analysis of microbial cells.

Figure 4A:
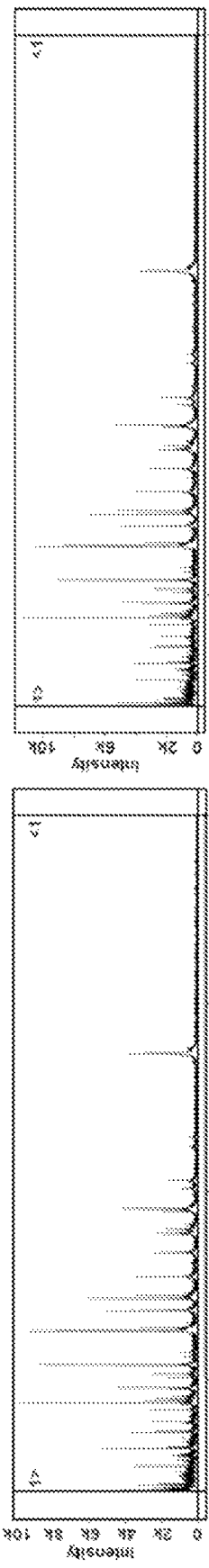
Figure 4A:
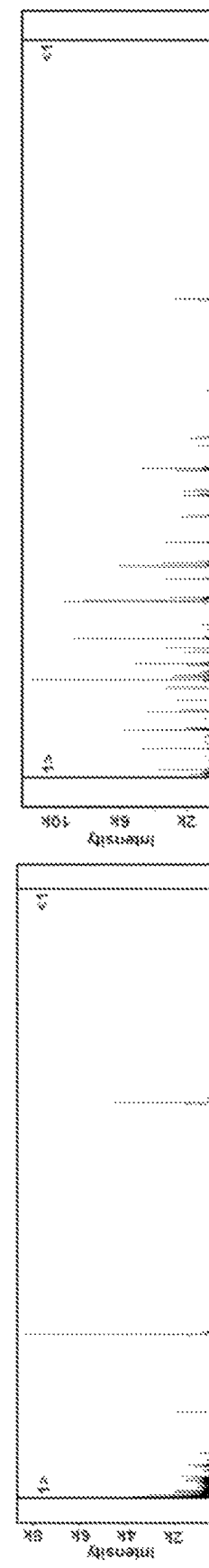
Figure 4B:
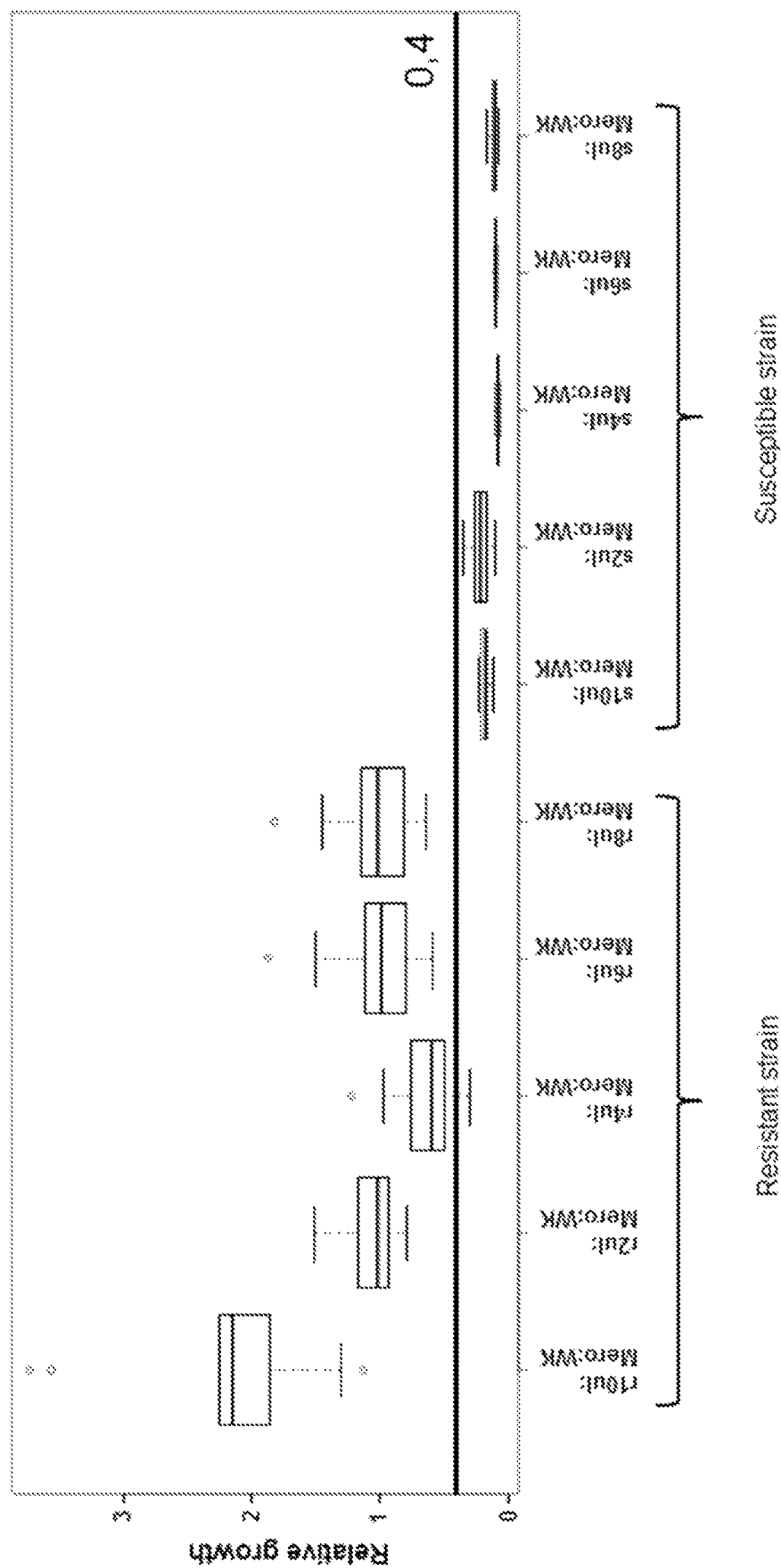

FIG. 4A and FIG. 4B present results of resistance/sensitivity testing according to the principles of the methods presented here.

FIG. 5A to FIG. 5I are schematics showing, by way of example, a method of preparation for microorganisms according to the second preferred aspect of the disclosure.

Figure 6:
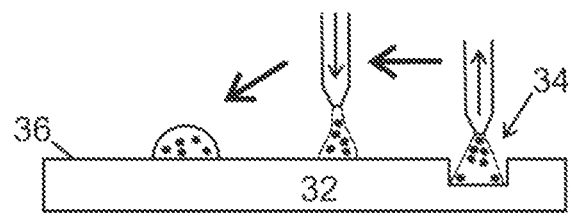

FIG. 6 illustrates an embodiment of a combined sample support with flat sections at one end, which can therefore be used as a mass spectrometric sample support (and if necessary for the preparation thereupon), and sections with embedded vessels at the other end for the cultivation/incubation of microorganisms in liquid nutrient media.

DETAILED DESCRIPTION

While the invention has been illustrated and explained with reference to a number of embodiments, those skilled in the art will recognize that various changes in form and detail can be made thereto without departing from the scope of the technical teaching as defined in the enclosed claims.

According to a first preferred aspect of the disclosure, it was surprisingly found that the preparation of a living, microbial sample directly on a mass spectrometric sample support can be used by itself for the cultivation of microorganisms to produce a sufficient number of microorganisms on the sample spot for the mass spectrometric detection. In this simple, but nevertheless surprisingly efficient embodiment, the droplet of nutrient medium in which the living microbial cells are suspended or immersed serves as a breeder reactor, as it were.

FIG. 2A to FIG. 2G are schematic illustrations of such a cultivation method in a droplet directly on the sample support with subsequent mass spectrometric measurement.

Figure 1:
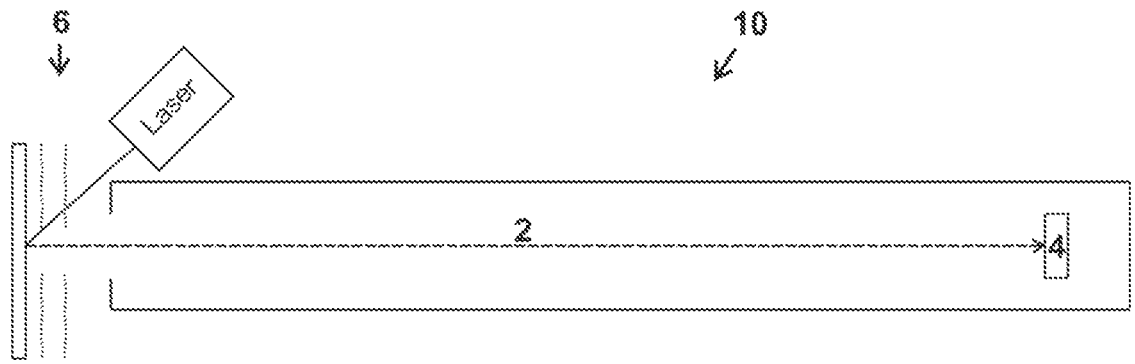
Figure 2A:
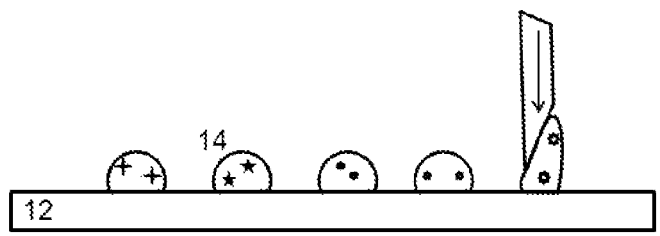
FIG. 2A to FIG. 2G are schematics showing, by way of example, a method of preparation for microorganisms in a microbial sample for the purpose of identification.

A flat sample support 12 is coated with droplets 14 of a microorganism suspension at different sites ("spots"). The liquid contains a nutrient medium such as a cation-adjusted Mueller-Hinton culture broth or an Iso-Sensitest culture broth. The droplets 14 can have a volume of 1-10 microliters, depending on the requirement, for example 2, 4, 6 or 8 microliters. The sample spots can be labeled on the support surface, or applied at positions with sufficient separation on an otherwise featureless surface of the support 12. An AnchorChip plate with 96 labeled spots can be used as the support 12, for example (Bruker Daltonik GmbH, Bremen, Germany). Alternatively, the sample spots can be defined by the droplet of nutrient medium 14 applied, which cannot spread out when the surface of the sample support 12 is sufficiently hydrophobic. FIG. 2A.

The support 12, which is coated in this example with five droplets 14 each containing different microorganisms, is placed in an incubation chamber 16, where it can be kept under a defined, controlled atmosphere of 36° C. and nearly 100% relative humidity, for example, for up to around 18 hours. It should be mentioned here that the application of the microbial samples can of course take place in the incubation chamber 16; the associated method steps of depositing the samples onto the sample support 12 and placing the sample support 12 in the incubation chamber 16 can thus reverse the order in all conceivable embodiments of the procedures described in this disclosure.

The humidity in the incubation chamber 16 can be set with a sodium chloride solution, for example. During their time in the incubation chamber 16, the microorganisms can multiply as they metabolize the nutrient medium in the droplets 14. The propagation can become visible by virtue of the fact that the originally clear nutrient medium in the droplet 14 becomes cloudy after a few hours (not shown).

Figure 2B:
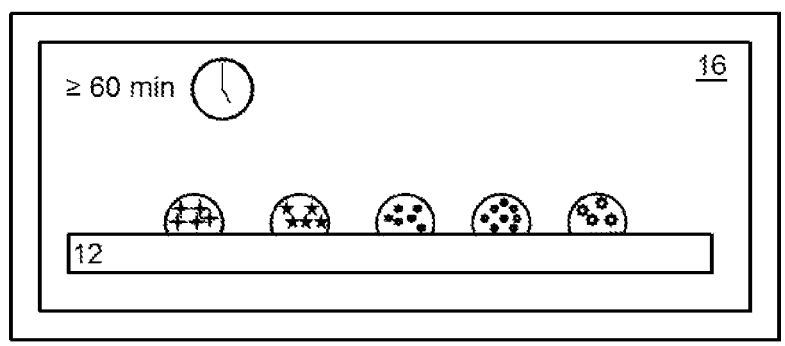
Figure 2C:
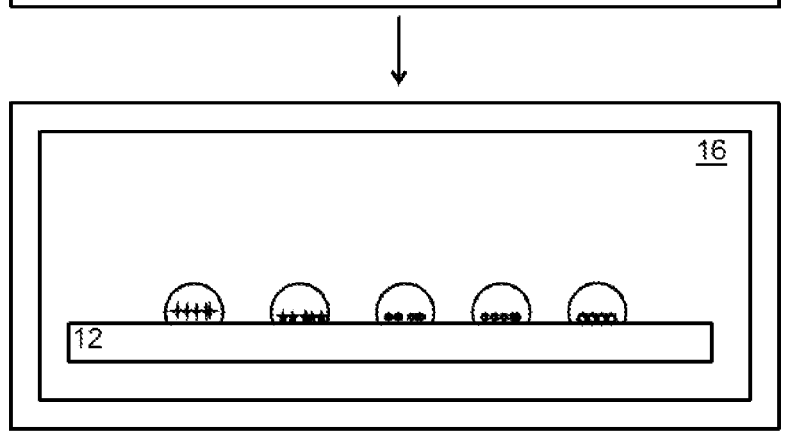

For microorganism growth which can be detected mass spectrometrically, it is not imperative that the medium becomes cloudy, however, but this can serve as a visual process control marker, given sufficiently long incubation times. FIG. 2B. The inventors surprisingly observed that, at the same time, the multiplied microorganisms settle in sufficient quantities at the boundary between droplet 14 and support surface, greatly facilitating the subsequent liquid reduction (dehumidification) or drying. FIG. 2C.

Figure 2D:
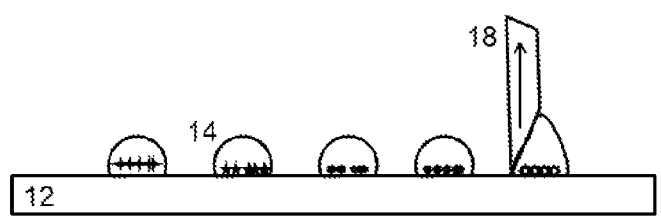
Figure 2E:
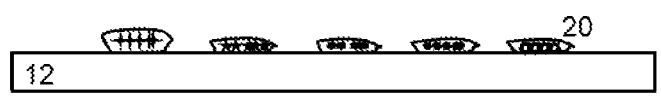

In one version, the residual liquid in the supernatant of the droplet can be carefully drawn off by means of a micropipette or a nanopipette 18 until the sedimented clumps of microbial cells 20 on the support surface are almost completely exposed. FIGS. 2D-2E. Surprisingly, the afore-described sedimentation behavior means that sufficient microorganisms remain on the sample spots after the residual liquid of the nutrient medium has been removed in this way, and thus the basis for the production of detectable mass signals in the detector of the mass spectrometer is maintained.

Figure 2F:
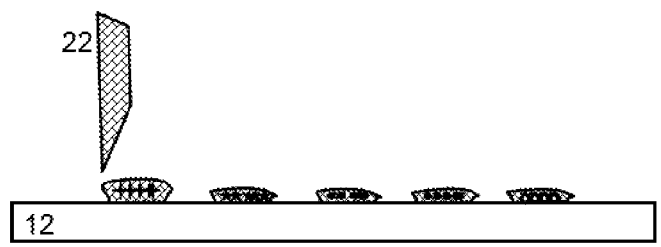
Figure 2G:
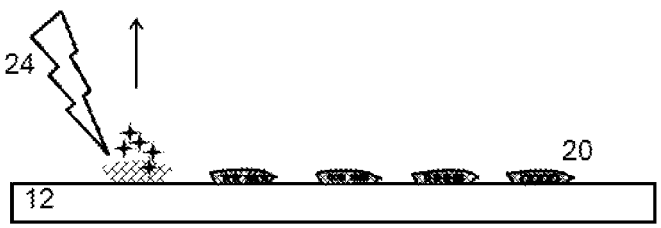

Afterwards, the exposed microorganism deposit 20 on the sample spots can be coated with a matrix substance for ionization by matrix-assisted laser desorption directly on the sample support 12 (pipette tip 22 with tile hatching). FIG. 2F. In addition, further preparatory steps such as the addition of substances for a protein/peptide extraction and/or a washing step can be inserted before this (not shown); they are well known to the specialist. In the ion source of the mass spectrometer, the sample spots thus prepared are bombarded with a laser 24, thus producing ions from the sedimented and prepared film of microorganisms 20 on the sample spot, which are fed to the connected mass analyzer to be measured. FIG. 2G.

The species or subspecies of the cultured microorganism can be derived with a high degree of reliability from the specific mass signals in the acquired mass spectra by means of known evaluation algorithms such as the MALDI Biotyper® (Bruker Daltonik GmbH, Bremen, Germany) by comparison with reference spectra from a spectral database. The procedure for such an evaluation is known to the specialist and does not need to be explained in more detail here.

In addition to the afore-described pure identification measurement after the microorganism has been cultured directly on the mass spectrometric sample support, the present disclosure also provides methods and test kits to prepare the microbial samples for resistance/sensitivity testing, as will be explained below.

The conventional devices for sensitivity testing normally test a large number of antibiotics simultaneously (for example 12 to 18), which are contained in standardized so-called "panels". The results are usually not available on the same working day, since they require longer incubation and reaction times; usual incubation period: 10-24 hours (so-called "overnight incubation"). In actual clinical situations, it can be sufficient to test only one or a few antibiotics which are specifically indicated with a particular patient and his illness, or which have already been administered to a particular patient. There can, however, be an urgent need to check the effectiveness, if, for example, no clinical improvement can be observed under antibiotic administration. It is very important here, particularly in the case of life-threatening infections such as sepsis, that the result of such a test is made available to the physician treating the patient not the next day, but within a significantly shorter period of only a few hours, for example, to help him to decide on a therapy.

For this reason, this description particularly focuses on methods and devices (test kits, consumables and other tools) for carrying out individual rapid tests, i.e. tests of a specific antibiotic against a certain microorganism or against groups of microorganisms. This does not preclude the use of the same or similar or derived principles, adjusted to the simultaneous testing of several antibiotics, where necessary, for the simultaneous or prompt testing of a large number of antibiotics.

One of the characteristics of the method described according to the first preferred aspect is the fact that the resistance/sensitivity test, or at least most of the procedural steps required, is performed directly on a mass spectrometric sample support such as a MALDI-TOF MS support, i.e. a flat and conductive plate suitable for this purpose, made of polished steel or ceramic, for example, which serves as the substrate of the ionization during the measurement in the ion source of a mass spectrometer. In the method described, the sensitivity testing is growth-based (culture-based), i.e. the method is a phenotypic sensitivity test and is thus independent of the underlying resistance mechanisms (if present).

The growth of the microorganisms with and without an antibiotic (the latter characterizes the growth control) can likewise take place directly on a MALDI-TOF MS support, on which the measurement subsequently takes place, also. This fundamentally distinguishes the method described according to the first preferred aspect from the existing MALDI-TOF MS based methods, where the microorganisms are cultured away from the MALDI-TOF MS support. With such methods, the cultivation with and without an antibiotic (for the growth control) takes place first in cultivation vessels or wells of microtitration plates, after which the microorganisms or the microbial proteins are isolated in these vessels or wells, and are subsequently transferred onto a MALDI-TOF MS support and then measured. This requires a series of labor-intensive manual steps, however, which means that it is difficult to integrate such methods into routine diagnostic work. The proposed method according to the first aspect allows a very much simpler and faster preparation of the samples, however.

In a similar way to FIG. 2A to FIG. 2G, the process steps described here are illustrated, by way of example, in FIG. 3A to FIG. 3H, which serve to schematically illustrate their possible meaning. However, practitioners in the field will recognize that certain process steps can be executed in a modified form. Persons skilled in the art will take the workflow proposed here as an aid to orientation and deviate from it, where appropriate, in line with their routine skills and knowledge, if this appears necessary or useful to them.

Figure 3A:
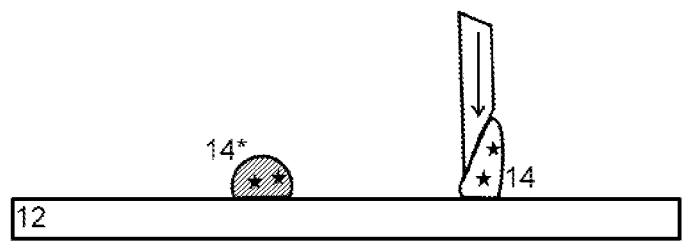
FIG. 3A to FIG. 3H are schematic illustrations of a possible method for resistance/sensitivity testing of a microbial sample.

The antibiotic (for example an antibiotic solution in a liquid nutrient medium) can be mixed with a microorganism suspension either in a cultivation vessel or directly on a spot of a MALDI-TOF MS support 12 (hatched droplet 14*). In addition, this is generally accompanied by a growth control on a different section of the MALDI-TOF MS support, i.e. a cultivation of the microorganism suspension in a nutrient medium without the addition of an antibiotic (unhatched droplet 14). It is preferable for a very small quantity of the suspension to be applied to the spots; for example 1-10 microliters. The sensitivity test thus takes place in microdroplets 14, 14*, preferably with a volume of around 4-8 microliters. The use of even smaller volumes is also possible in principle, for example in the form of nanodroplets. The initial microorganism concentration in the droplets 14, 14* can be slightly below the detection limit of a conventional MALDI time-of-flight mass spectrometer with linear flight path, and thus amount to around $5 \times 10^5$ cfu per milliliter, for example (cfu—colony forming unit). FIG. 3A.

Figure 3B:
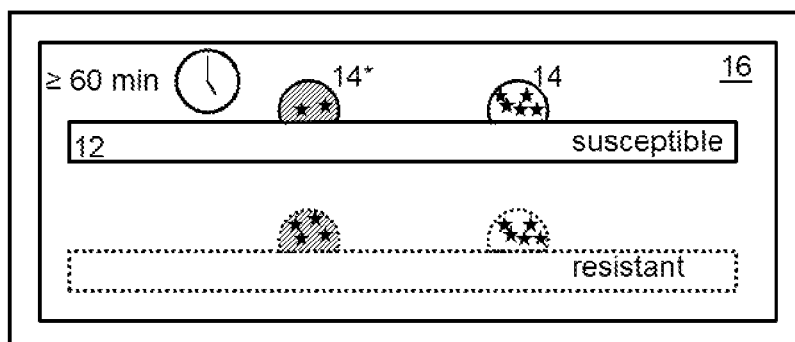

In the example shown, the MALDI-TOF MS support 12 with the test solution is subsequently cultured in a so-called "humidity chamber" 16 in an incubator at high humidity. The purpose of the humidity chamber 16 is to prevent the droplets 14, 14* from evaporating prematurely during the incubation, and it can take the form of a box with a lid, made of plastic, for example, into which the MALDI-TOF MS support can easily be placed. This humidity chamber 16 can have a form similar to that of the customary transport or storage containers for commercial MALDI-TOF MS supports (Bruker Daltonik GmbH, Bremen, Germany) and is preferably designed such that the MALDI-TOF MS support 12 here can be placed deep enough inside it so that the lid does not make contact with the droplets 14, 14* on the surface of the MALDI-TOF MS support 12. A small quantity of liquid can be put in the humidity chamber 16, for example 0.1 to 5 milliliters of water or NaCl solution to humidify the atmosphere in the chamber 16 and thus set a high ambient humidity (nearly 100%) so that the evaporation of the droplets of nutrient medium 14, 14* themselves is prevented. FIG. 3B.

In the droplets 14, 14*, a high concentration of the microorganisms in a small volume of liquid is rapidly achieved during incubation (as long as the growth is not inhibited by antimicrobial substances). After a sufficient period of time, the humidity chamber 16 with the MALDI-TOF MS support 12 can be removed from the incubation cabinet (not shown). The MALDI-TOF MS support 12 is then removed from the humidity chamber 16 and the droplets 14, 14* on the support are dried. The drying can be passive, in air for example, or accelerated for example by an actively produced airflow, the effect of heat, a combination of both, or other methods. The drying occurs very rapidly because of the very small volume of liquid in a droplet 14, 14* (nanoliters to microliters). However, this simple drying of the droplets (for example with hot air) can have the disadvantage that not only the microbial cells but also proteins and other components of the liquid nutrient medium become enriched on the spots of the MALDI-TOF MS support 12 and interfere with the MALDI-TOF MS measurement. This potential problem can be remedied by separating the microbial cells from the nutrient medium directly on the MALDI-TOF MS support 12.

Figure 3C:
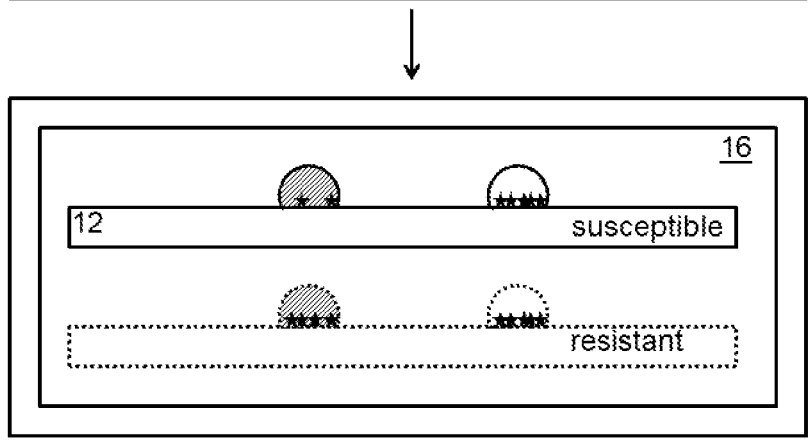

In both cases of drying and separating, the objective is to largely remove the residual liquid of the droplet of nutrient medium 14, 14* in order to prepare the sample spot for the subsequent preparation. As intimated above, the inventors have ascertained during their investigations that the microbial cells appear to have the tendency to sediment during the incubation, which can take several hours, and to then predominantly accumulate directly on the surface of the MALDI-TOF MS support 12. To a certain extent, the cells even adhere ("stick") to the surface of the support 12 and form a kind of "microorganism biofilm", whereas liquid constituents form a "supernatant" positioned above it. Without wishing to provide a complete scientific explanation for this behavior as microorganisms grow in a droplet on a flat plate, it is assumed that physical interactions between the plate surface and the microorganism cells, and adhesion processes arising from the biochemical and biophysical properties of the surface of the microorganism cell, are responsible for the pronounced deposit-forming. FIG. 3C.

Figure 3D:
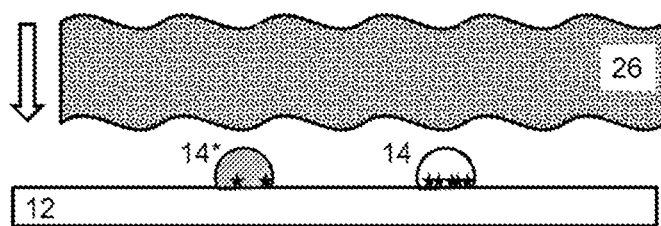
Figure 3E:
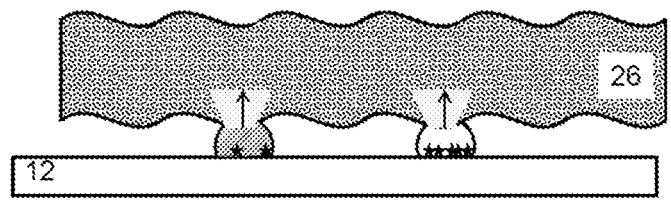
Figure 3F:
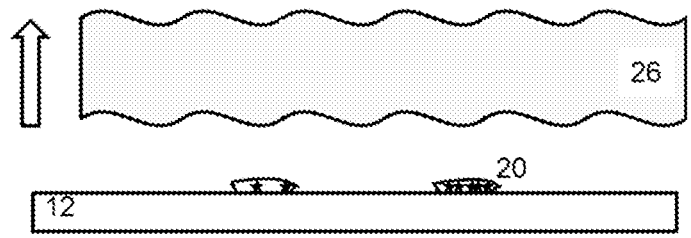

Exploiting this new finding, the supernatant liquid nutrient medium (residual liquid) can be pipetted off from the droplets 14, 14* on the MALDI-TOF MS support 12, as has already been described with reference to FIG. 2D in a different context. Alternatively, the liquid can simply be dabbed off to expose the microorganism deposit from liquid. Absorbent, low-linting wipes 26 can be used for this purpose, for example, as are commonly used in biology/chemistry laboratories; for example KimWipes™. The separation here takes place immediately and can be explained by the capillary effect, amongst other factors. The separation can be undertaken by manually dabbing with a folded cloth, for example (such as absorbent paper, blotting paper, soft cloths for cleaning sensitive surfaces) or with the aid of a special device. Such a device can have a sheet or pad of an absorbent material, for example, which, for uniform, rapid and standardized dabbing in particular, is simply positioned above the MALDI-TOF MS support 12 close enough to allow a fluid contact to be established with the droplets 14, 14*, and removed again after a relatively short absorbing time of a few seconds. FIGS. 3D-3F.

In an alternative embodiment of the dabbing, the contact between droplet and absorbent fabric is not established in the vertical direction (perpendicular to the sample support surface, as shown in FIGS. 3D-3F), but at the lateral edge of the droplet or droplets, close to the surface of the sample support. This makes it possible to ensure that (i) the residual liquid of the nutrient medium is absorbed faster and more completely, and (ii) the cells, which preferentially accumulate in the center of the spot at the surface, never come into contact with the absorbent fabric so that the danger of unintended cell removal is reduced. This modification of the liquid absorption can further reduce the background in the mass spectra and thus improve the quality of the measurements even more.

These versions of the removal of residual liquid explained above also result in a largely dehumidified (or depleted of residual liquid, exposed) microorganism deposit 20 with few remnants of the potentially interfering nutrient medium on the corresponding sample spot. This deposit serves as the basis for the subsequent mass spectrometric measurement.

Separating the cells from the liquid nutrient medium by dabbing or pipetting off the liquid as described here results in very effective measurements with high quality MS spectra. A further advantage of this separation compared to the (passive) drying of the droplets is that the separation takes place extremely quickly (immediately or instantly), which provides a definite time saving and allows the further processing of the samples to take place immediately. The dabbing can nevertheless be accompanied by a heated, drying airflow in certain embodiments in order to deplete the residual liquid even more thoroughly.

The method described for separating cells from a liquid medium is similarly effective to centrifugation with subsequent removal of the supernatant, but can be carried out directly on a MALDI-TOF MS support without taking any additional time. The separation effect can be enhanced still further—for example by using special MALDI-TOF MS supports, such as anchor supports (AnchorChip, Bruker Daltonik GmbH, Bremen), for example, or MALDI-TOF MS supports with individual sample spots in the form of a flattened cone. Shallow, but slightly conical wells could enhance the cell sedimentation effect. Other methods of washing liquid samples directly on a support can be used also.

To enhance the formation of a microorganism deposit (adhesion) on the sample support surface during the growth phase, the spot surfaces can be coated with different adhesion-promoting substances, for example proteins or sugars. These substances are preferably chosen such that they do not interfere with the measurement and/or the comparison of the microbial mass spectra with reference data sets. This can be achieved, for example, by having the mass signals of these substances outside the mass range to be evaluated, which is usually between m/z 2,000 and m/z 20,000, such as between m/z 3,000 and m/z 15,000, for example. Alternatively, substances with adhesion-promoting properties (for example, proteins) can be chosen which can simultaneously be used as standard substances; i.e. as markers for the good quality of the measurement and/or as intensity markers. In this case, the mass signals of these standard substances can be in the mass range to be evaluated. Furthermore, materials with enhanced adhesion characteristics and/or an enhanced surface finish can be used from the outset as materials for the manufacture of the MALDI-TOF MS supports.

Figure 3G:
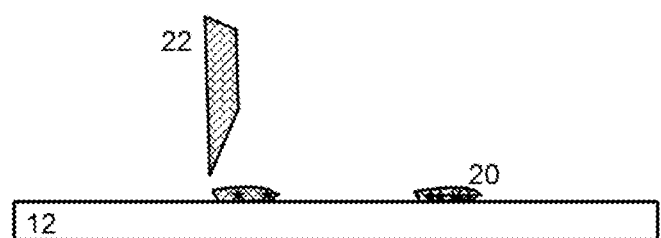
Figure 3H:
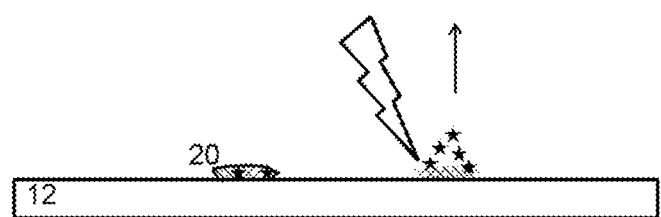

After drying or separating the droplets of the liquid nutrient medium on the corresponding spots, the spots are coated with a matrix for MALDI-TOF MS analyses (pipette tip 22 with tile hatching), for example, before the support is introduced into the MALDI-TOF MS instrument and the microbial biomolecules, for example proteins or peptides, are measured, as already explained above. FIGS. 3G-3H.

Before or at the same time as the matrix substance is applied, different substances, for example formic acid or acetonitrile, can be added to improve the extraction of the microbial proteins, and these substances aid the measurement (not shown). Droplets of de-ionized water can also be applied to the microorganism deposit as washing droplets and removed again to remove salts. After the measurement, the results can be evaluated in accordance with the algorithms, which are explained in more detail below. This involves assessing and rating the growth of the microorganisms in the presence of antibiotics. The fundamental principle here is that the growth of the sensitive microorganisms is inhibited in the presence of the antibiotics, while the resistant microorganisms are able to grow despite the antibiotic. The inclusion of a growth control, i.e. a test of the microorganism suspension without antibiotic on the same MS sample support, can be helpful for the evaluation and for the corresponding evaluation algorithms. FIG. 3B and FIG. 3C schematically show the growth and the sedimentation behavior for sensitivity (solid line) and resistance (broken line) by way of comparison.

In one version of the method, the microorganisms can be cultured with and without antibiotic on a composite microtitration plate, where a flat, plane mass spectrometric sample support, such as a MALDI-TOF MS support, forms the bottom and, together with a removable top part containing through-holes, provides a grid of wells, as described in the patent application CA 2 467 131 A1 (FIG. 10 there). The reaction vessels or wells provided can (for example as a test kit) already contain antibiotics in the form of a solution, a powder, or in a lyophilized form, for example, before a microorganism suspension is added. After a sufficient incubation period accompanied by, or in the absence of, microorganism growth, the residual liquid of the droplets is removed, for example by drying, and the top part is removed from the MALDI-TOF MS plate. This can then be followed by MALDI matrix preparation, as described above, and MALDI-TOF MS measurement.

In a further embodiment, the MALDI-TOF MS support is not incubated in a separate incubator, but the incubation function can be integrated directly into the MALDI-TOF mass spectrometer or into the complete system, for example in the form of an incubation unit or an incubation module. This allows automation and a further reduction in the manual preparation steps which are necessary. A further embodiment provides for the integration of a heating device in the humidity chamber itself, which can then assume the function of an incubator, obviating the need to provide a separate incubator.

The use of mass spectrometric sample supports which are already pre-processed with antibiotics on the spots in the form of a dry powder, or in a different form, can additionally make it easier for the user to perform the sensitivity testing.

FIG. 4A shows results of a resistance/sensitivity test using the example of the facultatively anaerobic, gram-negative rod bacterium *Klebsiella pneumoniae* against the β-lactam antibiotic meropenem from the group of carbapenems. The sample preparation was carried out directly on the sample support, as described schematically in FIGS. 3A-3H. The volume of the droplets dispensed was six microliters; the concentration of the antibiotic was 2 micrograms per milliliter; and the dwell time in the appropriately conditioned incubation chamber was four hours. MALDI time-of-flight mass spectra were evaluated with the software module of the commercial product MALDI Biotyper®. One meropenem-resistant strain (mass spectra at the top) and one meropenem-sensitive strain (mass spectra at the bottom) of the bacterium were tested, respectively. The growth control without any antibiotic, which was prepared on the same MALDI sample support plate, is shown in the spectrum on the right in each case.

It can be clearly seen that in the case of the resistant strain, the signatures of specific mass signals in the two top spectra differ hardly at all. It is thus possible to conclude that it is resistant, since the bacterial growth is obviously not inhibited in the presence of meropenem, and a reliable identification of the species is possible. In the case of the sensitive strain, on the other hand, specific mass signal signatures can only be seen in the spectrum of the growth control (bottom right). In the presence of meropenem (spectrum bottom left), however, the *Klebsiella* cells obviously cannot multiply (or scarcely). The individual mass signals which stand out in the bottom left spectrum belong to a reference substance which is added to the droplet of nutrient medium for the purpose of microorganism quantification, but are not taken into account in the investigation specifically described here. Under these conditions of a lack of growth, the evaluation software is not able to determine the species of microorganism due to a lack of data; this is true particularly when the initial quantity of microbial biomass is below the mass spectrometric detection limit. This permits the conclusion to be drawn that this *Klebsiella* strain reacts sensitively to this specific antimicrobial substance.

FIG. 4B uses a bar chart to illustrate a statistic of the growth behavior of *Klebsiella pneumoniae* in the presence of meropenem from the experiment in FIG. 4A over five different droplet sizes 2, 4, 6, 8 and 10 microliters. As can be seen, the relative growth of the sensitive strain is reliably below the significant growth threshold of 0.4, whereas for the resistant strain it is far above the threshold, with the one exception of the 4 microliter droplet, where although the median is significantly greater than 0.4, measurements occasionally occur below it.

The resistance/sensitivity test can be carried out on microbial samples obtained from cultures or directly from biological material. In the Prior Art, mature cultures are typically used for sensitivity testing, which have been incubated for 16-24 hours on a solid medium such as agar, and are present in the form of developed colonies after such incubation times. Testing from mature cultures incubated in a liquid nutrient medium is also possible.

In many situations, however, it is advantageous to already perform a sensitivity test directly from the material to be analyzed in order to significantly reduce the time until the result is available. Positive blood cultures can be cited as an example for such a material where fast pathogen diagnosis is of crucial significance. Nowadays, the procedure in blood culture diagnostics is usually such that the blood samples taken from the patient are first put into special blood culture bottles with liquid nutrient medium. These bottles are subsequently read into automated incubators which continuously monitor the bottles for any microbial growth which may occur, by measuring carbon dioxide, for example. When there is a positive report from a blood culture bottle, the liquid from it is smeared onto solid media, and the latter are then incubated usually for 16-24 hours. The colonies resulting from this are used for the identification and for antibiotics sensitivity testing. The colonies are also suitable for the method of sensitivity testing described here, among other things.

However, identification and sensitivity testing directly from blood cultures that are reported to be positive save the time needed for cultivation on solid media, and thus allow the result to be obtained approx. one day earlier. To achieve this, the sample must undergo preparatory processing to enrich the microorganisms. This can be achieved by a lysis/centrifugation method or lysis/filtration method, for example. With the lysis/centrifugation method, the blood cells are first lysed by adding a lysing agent such as a tenside, for example, before the microorganisms are concentrated by centrifugation. In an optional washing step, a washing buffer is added and the microorganisms are concentrated again by centrifugation. The identification is then carried out immediately or after a protein extraction. Such a method for the identification has been developed as a MALDI Sepsityper® identification kit (Bruker Daltonik GmbH, Bremen, Germany) and is commercially available (N. G. Morgenthaler et al., International Journal of Microbiology Volume 2015, Article ID 827416, 10 pages).

This or similar methods can likewise be used as the preparatory processing of the samples (enrichment of the microorganisms) for the resistance/sensitivity testing by means of MALDI-TOF MS described here. This significantly reduces the time until the result is obtained.

Alternatively, sub-cultures from positive blood cultures or other materials which have been incubated very briefly on a solid medium can be used for the MALDI-TOF MS-based sensitivity test described here. The use of sub-cultures from positive blood cultures incubated very briefly on a solid medium was recently demonstrated for the identification (Idelevich et al., Clin Microbiol Infect. 2014; 20:1001-1006) and sensitivity testing (Idelevich et al., J Clin Microbiol. 2014; 52:4058-4062). Here, the solid media are incubated after sub-cultivation (smearing) only briefly, usually 1.5 to 6 hours, and the "young" microbial biomass thus produced is used for the identification and sensitivity test. Although this procedure does not allow a direct test immediately after a blood culture has been registered positive, it is nevertheless very fast compared to conventional testing from mature colonies incubated for 16-24 hours. The advantage of this method consists in the fact that no additional consumables or additional work are necessary; the solid media have simply to be observed at an earlier stage and testing is carried out from the "young" biomass.

Particularly advantageous is sensitivity testing directly from blood without previous incubation of the blood samples in a blood culture machine. The preparatory processing of the samples to propagate the microorganisms can be carried out as described above for the testing from blood cultures recorded as positive.

Whereas a direct MALDI-TOF MS-based identification directly from blood is currently difficult to perform even after the microorganisms have been concentrated due to the low concentrations of the microorganism cells in blood without prior culturing, a direct MALDI-TOF MS-based sensitivity test directly from blood is possible by means of the method described here. After isolating the microorganisms from the blood, a microorganism suspension is prepared in a liquid nutrient fluid and, as is usual with sensitivity testing, mixed with an antibiotic. This suspension and, if used, a growth control is then applied in the form of droplets onto a MALDI-TOF MS support, where it is incubated directly. Even with very low initial microbial cell counts in the blood, the microorganisms will multiply after a certain incubation period, at least in the growth control or, if a phenotypic resistance exists, in the mixture of sample and antibiotic, too. This can be detected by the MALDI-TOF mass spectrometer. The sensitivity testing is therefore in effect carried out according to the same principle as described in relation to the first preferred aspect of this disclosure.

Microorganisms from mature colonies incubated on solid media can easily be identified by means of MALDI-TOF. The samples do have to undergo preparatory processing for a direct identification from material under investigation (for example from positive blood cultures), however. This is possible with the above-described lysis/centrifugation method, for example. This method requires additional processing steps, however, which are time-consuming and make it more difficult to integrate it into routine laboratory diagnostics.

The methods described in this application for the detection and identification from droplets, or for sensitivity testing in droplets directly on a MALDI-TOF MS support according to the first preferred aspect, can be carried out not only in isolation, but also in combination. Such a combination particularly makes sense when testing directly from the material under investigation, from positive blood cultures, for example. By combining sensitivity testing with identification in this way, the MALDI-TOF MS measurement not only compares the growth of the control measurement with the growth of the sample with added antibiotic in accordance with the algorithms described for sensitivity testing, but the uninhibited microbial growth in the control measurement can additionally be used for the usual MALDI-TOF MS identification. When the incubation periods are sufficiently long, but still very short compared to usual incubation periods of 16-24 hours, the quantity of microbial biomass is sufficient for the identification. The advantages of this combined method are that (i) it is possible to forgo additional processing steps for the lysis/centrifugation method, for example, (ii) the results of sensitivity testing and identification are available promptly and simultaneously, and (iii) the time until the sensitivity testing and identification are completed is shorter compared to conventional testing from mature colonies.

This combined method can be applied to testing from mature or young colonies as well as testing directly from material, for example from a positive blood culture or blood.

A further embodiment of the methods described here enables fast and simple detection of resistance mechanisms of microorganisms. This is achieved by combination testing, for example. That is to say, a suspension comprising microorganism, antibiotic and a substance which specifically cancels out a possible resistance of the microbial organism to the antibiotic (i.e. based on a specific resistance mechanism) is tested in addition to the suspension comprising the microorganism and antibiotic, and a suspension comprising only the microorganism (growth control without antibiotic).

One example for this is the detection of the formation of β-lactamases by bacteria. β-lactamases are bacterial enzymes which can cleave β-lactam antibiotics and thus render them ineffective. Examples of β-lactamases are ampC-β-lactamases, Extended Spectrum β-lactamases (ESBL), carbapenemases and others. Each type of β-lactamase cleaves a specific spectrum of antibiotics, and moreover has different properties (for example localization of the gene on a plasmid or on the chromosome), which limit the range of antibiotics available for a therapy to different extents and allow bacterial strains to have different propagation speeds. A rapid determination of the underlying resistance mechanism can thus be very important, and especially in the context of investigations into hospital hygiene and hygiene measures which may need to be introduced.

By adding a specific β-lactamase inhibitor (for example clavulanic acid for ESBL, or vaborbactam for meropenem), the effect of a β-lactamase can be specifically neutralized. This principle is not only exploited therapeutically, but also diagnostically for the detection of the β lactamase, which underlies the resistance. For example, test disks impregnated with antibiotic and test disks impregnated with antibiotic plus β-lactamase inhibitor are commercially available. After the bacterial culture has been smeared out on a solid medium such as an agar plate, these test disks are applied; and after 16-24 hours, the zones of inhibition are measured (agar diffusion test). If a specific difference in the zone of inhibition diameter between the test disks with antibiotic and the test disks with antibiotic plus the β-lactamase inhibitor is reached, this indicates the production of a specific β-lactamase.

Apart from being simpler to perform, the advantage of the methods described here for the combination tests is, in particular, that the result is ready after only a few hours, compared to the result of the agar diffusion method, for example, which requires much longer than 12 hours, and therefore is only available very much later on the next day. The speed advantage of the methods described here results from the fact that, firstly, the growth of the microorganisms in a liquid nutrient medium is significantly faster than on a solid medium, and secondly a high microorganism concentration is quickly achieved in a droplet because of the low volume of liquid. Thirdly, the mass spectrometric measurement, for example by MALDI-TOF MS, guarantees a more sensitive and more rapid growth detection than can be achieved by visual observation of the growth on a solid medium, as is the case with the agar diffusion method.

Compared to the identification of β-lactamases by detecting the β-lactam cleavage by means of MALDI-TOF MS (mass signals of uncleaved β-lactam or cleavage products), which was described at the start, the MALDI-TOF MS-based method described here using the combination tests has an important advantage: Detection of the β-lactam cleavage is an indirect method, i.e. in the positive case it is shown that a β-lactam antibiotic is cleaved, and from this it is concluded that the antibiotic will not be effective for this bacterial strain. However, the effectiveness can also depend on other factors, such as the dosage of the antibiotic. For the combination test described here, the effect of the β-lactamase inhibitor on the growth of the microorganism is additionally determined directly, i.e. whether the resistance is neutralized or not. Such results are of considerably greater clinical relevance.

Following the previous explanations, the combination tests described here can be used for the testing from mature or young colonies and also for testing directly from material, for example from a positive blood culture or blood.

Apart from applying the methods described in the form of individual high-speed tests, i.e. the testing of a specific antibiotic against a specific microorganism, it is also possible to test several antibiotics simultaneously (multiplex testing). This has the advantage that a complete antibiogram for the microorganisms in the microbial sample can be generated at the same time. Moreover, it is possible to simultaneously test several concentrations for each antibiotic, which allows the minimum inhibitory concentration (MIC) to be determined. MIC is the minimum concentration of an antibiotic which inhibits microbial growth. The MIC is a measure of the sensitivity of microorganisms to antibiotics. Firstly, the MIC allows a categorization of a microorganism into the categories "sensitive", "intermediate" or "resistant"; secondly, the MIC provides information on the "degree of sensitivity" of a microorganism to a specific antibiotic. For multiple testing, many spots of a MALDI-TOF MS support can be coated in parallel. Supports with 96, 384 or 1536 spots can be used, for example.

The growth of the microorganisms can be determined with different evaluation algorithms. The growth of the microorganisms with antibiotic can be compared with the growth of the microorganisms without antibiotic (growth control).

The detection of the microbial biomass is proposed as a possible algorithm. A specific lower detection limit is characteristic for the MALDI-TOF MS method, i.e. the minimum amount of microbial biomass (around $10^4$ or $10^5$ microbial cells per spot) which permits detection in the sense of generating recognizable mass signals in the mass spectrum. This lower detection limit depends on many factors, including the instrument characteristics and settings. According to the algorithm described here, a microorganism in the liquid nutrient medium can be applied to a spot in a concentration (quantity) which is below the lower detection limit of the MALDI-TOF MS measurement method. That is to say, if a MALDI-TOF MS measurement was to be carried out without further processing of this microbial sample, it would not be possible to detect any microorganism signature in the mass spectrum above the omnipresent background. From this it follows directly that if the microorganism is sensitive to the antibiotic being tested, the growth is inhibited and the microbial biomass will be almost undetectable even after the incubation period, since the lower detection limit is not exceeded. If, on the other hand, the microorganism is resistant to the antibiotic being tested, the microorganisms can grow during the incubation just as they can in the growth control (without antibiotic), and the microbial mass can be detected, i.e. corresponding specific microbial mass signals in the mass spectrum are detected.

To increase the accuracy of the method and avoid the probability of misinterpreting a "randomly" occurring signature in the mass spectrum which is similar to a specific microbial mass signal signature, even for small quantities of microbial biomass (normally below the detection limit), the quantification (possibly additionally in combination) or the relative quantification of the amount of microbial biomass can be used. This can be achieved for example by a comparison of the so-called "Area Under the Curve" (AUC) and/or peak intensities by using an internal standard ("MBT-ASTRA", Bruker Daltonik GmbH, Bremen, Germany) or by other statistical methods, which are well known to the specialist and do not have to be explained in more detail here. In particular, the reference data set for comparison with a microbial mass signature in the mass spectrum acquired can be derived or determined from the mass signals of an internal standard or a reference substance in the same mass spectrum.

The algorithm of the spatial resolution is proposed as another possible version. Here, MALDI-TOF MS methods are used to fire the laser shots in a precisely defined spatial grid—for example 1,000 shots distributed over defined areas of a prepared spot of a MALDI-TOF MS support. The number of "successful" shots, i.e. shots where a mass spectrum with detectable microorganism signature was generated, is compared between the microbial sample with antibiotic and the microbial sample without antibiotic (growth control), for example.

This algorithm can, for example, also be used as a supplement to the above-described algorithm for the detection of the microbial biomass in order to increase the accuracy of the detection method and reduce the probability of "randomly" occurring signatures in the mass spectrum itself even for small quantities of the microbial biomass (normally below the detection limit) being misinterpreted as significant growth. That is to say, a small number of successful shots cannot be interpreted as growth, for example, but is deemed to be random and not significant.

FIG. 5A to FIG. 5I explain an example embodiment of a method according to a second preferred aspect of the disclosure. Since many steps are similar to those of the aforementioned methods, and therefore the explanations regarding these methods can also be applied to this example, the following description is limited in all due brevity to the essential differences from the methods according to the first preferred aspect of the disclosure.

Figure 5A:
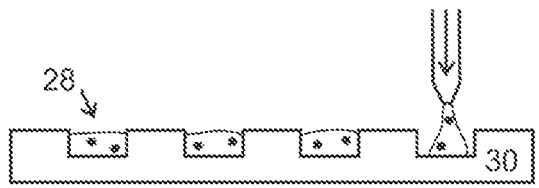

An essential difference is that the cultivation/incubation of microorganisms and the preparation for a mass spectrometric measurement are not carried out on the same flat substrate, such as a mass spectrometric sample support, but on separate substrates (or substrate sections). A microorganism suspension in a liquid nutrient medium is added to vessels 28; for example wells in a microtitration plate 30. The inoculum can be around $10^6$ cfu per milliliter; the volume of the nutrient medium around 50 to 250 microliters, preferably 100 microliters. For resistance/sensitivity testing, the wells 28 can (for example as a test kit) already contain antimicrobial substances, for example, in the form of a solution, a powder, or in a lyophilized form before a microorganism suspension is added Alternatively, these antibiotics can also be added to the nutrient medium at a later stage. FIG. 5A.

Figure 5B:
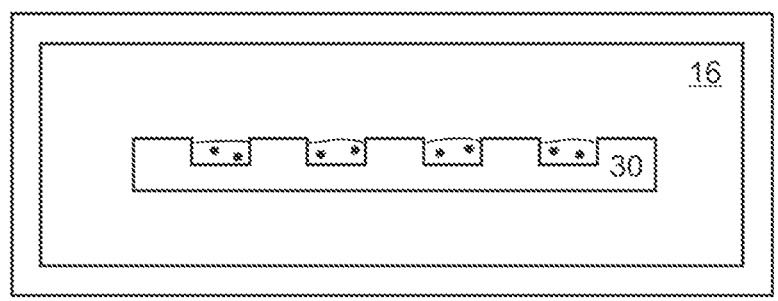
Figure 5C:
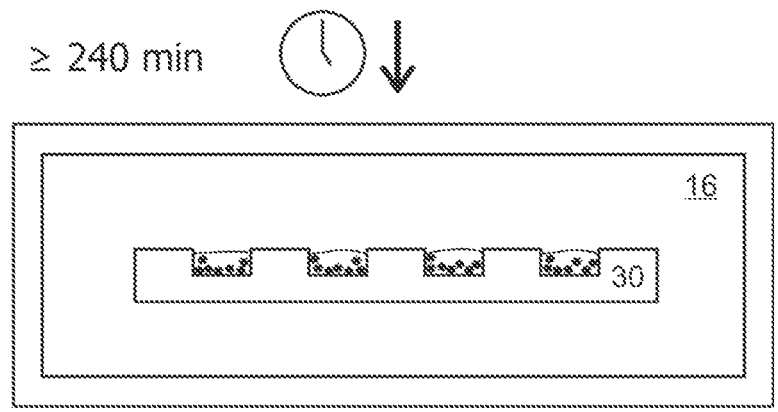

The well plate 30 is placed in an incubator 16 and kept there for a specific incubation period of 4 to 18 hours, for example, to promote the microorganism growth. As has already been explained, the microorganisms have a tendency to form deposits ("microorganism biofilm") at the bottom and on the lower part of the sidewalls of the wells 28. FIGS. 5B-5C.

Figure 5D:
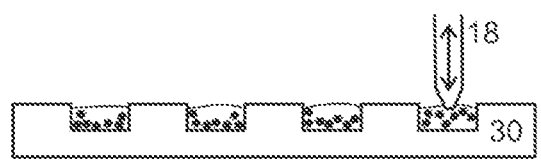
Figure 5E:
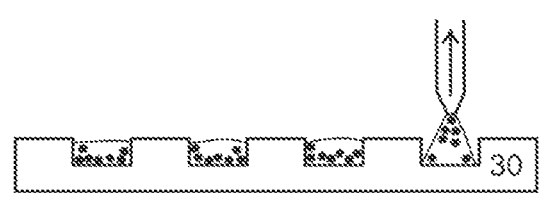

The well plate 30 is removed from the incubator 16. In order to remove a volume of nutrient medium with a sufficient quantity of intact, grown microorganisms from an approximately uniform microorganism distribution from the wells 28, the deposit can be agitated, for example by several up and down movements of the pipetting tip 18 or gentle agitation of the well plate 30, shortly before removal so that the microorganisms can be sampled in a greater concentration and uniformly distributed with the liquid of the nutrient medium. The quantity of liquid removed can be between 1 and 10 microliters. FIGS. 5D-5E.

As an alternative to this procedure, the formation of a microorganism deposit in the wells 28 during the cultivation can be hindered or prevented from the outset by carefully agitating the well plate 30 during its time in the incubator 16 (not shown). This can obviate the need for dispersing with the aid of the pipette tip 18 and/or subsequent agitation.

Figure 5F:
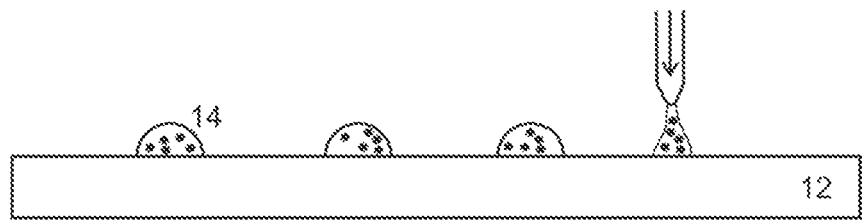

The liquid removed with the intact microorganisms contained therein is deposited as a droplet 14 on the spot of a flat mass spectrometric sample support 12. FIG. 5F.

Figure 5G:
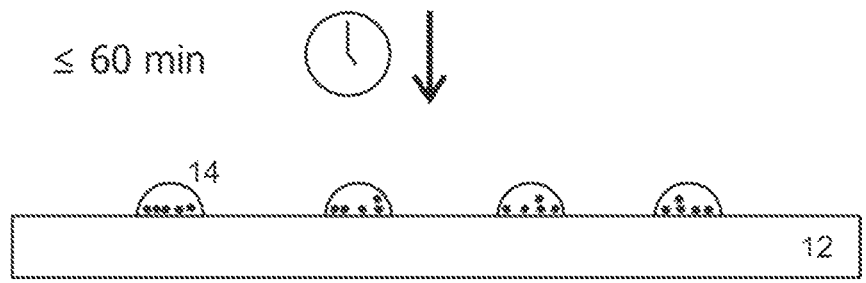

There then follows a standing or resting period of around 10 to 60 minutes, which affords the microorganisms an opportunity to accumulate or sediment at the interface between the droplet liquid and the support surface. The fundamental principle is that with increasing microorganism concentration in the droplet 14 on the sample support 12, the resting period can be shortened; in other words: at a high concentration, the resting period can be at the lower end of the preferred range; at a low concentration, it can be advantageous to wait for a longer time. FIG. 5G.

Figure 5H:

As has been explained above in a different context, the residual liquid of the nutrient medium can be removed from the sample spot after the resting period, for example by means of an absorbent fabric (cloth 26), which is laterally brought into fluid contact with the droplet 14 on a spot at the support surface and simply absorbs a large portion of the liquid. Other types of liquid removal such as pipetting off can be used, of course, as has been described above. FIG. 5H.

Figure 5I:
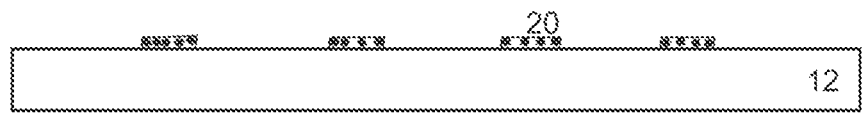

The microorganism deposit 20 exposed in this way can now be prepared further as described above and measured in a mass spectrometer. For example, peptides/proteins of the microorganisms can be extracted and/or the deposit 20 can be washed and/or the deposit 20 can be embedded into a MALDI matrix substance. FIG. 5I.

FIG. 6 illustrates schematically and by way of example a combined well/sample support plate 32 with a well 34 (which can represent a multitude of wells), in which the microorganisms can be cultured, and one flat section 36 with sample spots at a distance therefrom, which can be used as a substrate for a mass spectrometric sample preparation. In the ion source of the mass spectrometer, the disturbance which the well 34 causes to the electric field can be reduced by flush covering the well 34 in advance, for example (not shown).

The principles described here are not necessarily limited to MALDI-TOF MS measurement methods, but can essentially be implemented with other detection or differentiation methods, too, such as other mass spectrometric detection methods or methods to determine the intrinsic fluorescence.

Further embodiments of the invention are conceivable in addition to the embodiments described by way of example. With knowledge of this disclosure, those skilled in the art can easily design further advantageous preparatory and mass spectrometric measurement methods for living, microbial samples and microorganisms, which are to be covered by the scope of protection of the claims.

The invention claimed is:

1. Method for the preparation of microorganisms for a subsequent mass spectrometric measurement, comprising the steps of:
   (a) providing a flat sample support having a plurality of sample spots;
   (b) depositing the microorganisms in a droplet of liquid nutrient medium, which comprises cation-adjusted Mueller-Hinton culture broth, on a first one of the sample spots;
   (c) maintaining the flat sample support for a predetermined resting period to allow a microorganism deposit to form on the first sample spot;
   (d) removing residual liquid of the droplet of nutrient medium after the predetermined resting period to expose the microorganism deposit;
   (e) preparing the first sample spot for a desorbing ionization;
   (f) transferring the sample support into a desorption ion source of a mass spectrometer, generating ions from the prepared first sample spot and acquiring a corresponding mass spectrum; and
   g) comparing the mass spectrum with a reference data set to determine at least one characteristic of the microorganisms.

2. The method according to claim 1, wherein the reference data set has reference spectra which are taken from a library of previously acquired mass spectra, and wherein the at least one characteristic from Step (g) comprises species or subspecies of the microorganisms.

3. The method according to claim 1, wherein the microorganisms, before being applied in Step (b), are cultured in a vessel away from the flat sample support in the liquid nutrient medium and subsequently transferred to the first sample spot.

4. The method according to claim 3, wherein the microorganisms are cultured in a plurality of vessels, and wherein a subset of said vessels contain a liquid nutrient medium with one of an antimicrobial substance and combination of antimicrobial substance and enzyme inhibitor.

5. The method according to claim 4, wherein the reference data set is a mass spectrum acquired from one of said plurality of sample spots, on which a microorganism deposit is located which originated from a liquid nutrient medium without the antimicrobial substance or the combination of antimicrobial substance and enzyme inhibitor, and wherein the at least one characteristic from Step (g) comprises a sensitivity of the microorganisms to the antimicrobial substance or the combination of antimicrobial substance and enzyme inhibitor.

6. The method according to claim 5, wherein the microorganisms are cultured in different vessels with liquid nutrient medium, each at a different concentration, and wherein the at least one characteristic from Step (g) comprises a minimum inhibitory concentration (MIC) of the antimicrobial substance to the microorganisms.

7. The method according to claim 4, wherein the at least one characteristic in Step (g) is derived from a difference in the microorganism growth.

8. The method according to claim 3, wherein, prior to being cultured, the microorganisms are dosed in the liquid nutrient medium such that a quantity of the microorganisms is below a detection limit of the mass spectrometric measurement by which the mass spectrum is acquired.

9. The method according to claim 8, wherein the concentration of the microorganisms in the liquid nutrient medium is $5\times10^5$ colony forming units (cfu) per milliliter.

10. The method according to claim 3, wherein the microorganisms are either (i) dispensed into the vessel as a suspension in the liquid nutrient medium or (ii) placed in the vessel in cellular form, after which liquid nutrient medium is added.

11. The method according to claim 3, wherein a well in a microtitration plate is used as the vessel.

12. The method according to claim 1, wherein the predetermined resting period in Step (c) is between 10 and 60 minutes.

13. The method according to claim 1, wherein removing residual liquid from the flat sample support in Step (d) comprises dabbing off a droplet supernatant with an absorbent material or pipetting off the supernatant.

14. The method according to claim 1, wherein the preparation in Step (e) comprises at least one of (i) a preparatory extraction of microbial proteins/peptides from the microorganism deposit on the flat sample support, (ii) washing the microorganism deposit, and (iii) embedding the microorganism deposit in a laser light-absorbing matrix substance to be subsequently ionized by matrix-assisted laser desorption (MALDI) in Step (f).

15. The method according to claim 1, wherein the mass spectrum in Step (f) is acquired with time-of-flight (TOF) dispersion.

16. The method according to claim 1, wherein ions are generated from the prepared first sample spot in Step (f) using one of (i) matrix-assisted laser desorption ionization (MALDI), (ii) desorption electrospray ionization (DESI), and (iii) secondary ion mass spectrometry (SIMS).

17. The method according to claim 1, wherein the droplet of nutrient medium in Step (b) has a volume of between 1 and 10 microliters.

18. The method according to claim 1, wherein the flat sample support is a conductive plate made of polished steel or ceramic, or a plate with anchor spots.

19. The method according to claim 1, wherein removing residual liquid in Step (d) uses a device which operates a sheet or pad of an absorbent material, which is positioned above the flat sample support close enough to allow a fluid contact to be established with the droplet, and then removed again after a predefined liquid absorbing time.

20. A method for the preparation of microorganisms for a subsequent mass spectrometric measurement, comprising the steps of:
(a) providing a flat sample support having a plurality of sample spots;
(b) depositing the microorganisms in a droplet of liquid nutrient medium on a first one of the sample spots, the liquid nutrient medium comprising culture broth consisting essentially of the following ingredients in grams per liter:
Hydrolysed casein: 11.0
Peptones: 3.0
Glucose: 2.0
Sodium chloride: 3.0
Soluble starch: 1.0
Disodium hydrogen phosphate: 2.0
Sodium acetate: 1.0
Magnesium glycerophosphate: 0.2
Calcium gluconate: 0.1
Cobaltous sulphate: 0.001
Cupric sulphate: 0.001
Zinc sulphate: 0.001
Ferrous sulphate: 0.001
Manganous chloride: 0.002
Menadione: 0.001
Cyanocobalamin: 0.001
L-Cysteine hydrochloride: 0.02
L-Tryptophan: 0.02
Pyridoxine: 0.003
Pantothenate: 0.003
Nicotinamide: 0.003
Biotin: 0.0003
Thiamine: 0.00004
Adenine: 0.01
Guanine: 0.01
Xanthine: 0.01
Uracil: 0.01;
(c) maintaining the flat sample support for a predetermined resting period to allow a microorganism deposit to form on the first sample spot;
(d) removing residual liquid of the droplet of nutrient medium after the predetermined resting period to expose the microorganism deposit;
(e) preparing the first sample spot for a desorbing ionization;
(f) transferring the sample support into a desorption ion source of a mass spectrometer, generating ions from the prepared first sample spot and acquiring a corresponding mass spectrum; and
g) comparing the mass spectrum with a reference data set to determine at least one characteristic of the microorganisms.

* * * * *